(12) United States Patent
Wolin

(10) Patent No.: US 7,989,420 B2
(45) Date of Patent: Aug. 2, 2011

(54) SMOOTH MUSCLE RELAXATION

(75) Inventor: Michael Wolin, White Plains, NY (US)

(73) Assignee: New York Medical College, Valhalla, NY (US)

( * ) Notice: Subject to any disclaimer, the term of this patent is extended or adjusted under 35 U.S.C. 154(b) by 540 days.

(21) Appl. No.: 12/225,750

(22) PCT Filed: Mar. 21, 2007

(86) PCT No.: PCT/US2007/007008
§ 371 (c)(1),
(2), (4) Date: Sep. 26, 2008

(87) PCT Pub. No.: WO2007/126653
PCT Pub. Date: Nov. 8, 2007

(65) Prior Publication Data
US 2010/0173826 A1  Jul. 8, 2010

Related U.S. Application Data

(60) Provisional application No. 60/786,368, filed on Mar. 28, 2006.

(51) Int. Cl.
*A61K 38/28* (2006.01)
*A61K 31/22* (2006.01)
*A61K 31/195* (2006.01)
*A61K 31/16* (2006.01)

(52) U.S. Cl. ......... 514/6.1; 514/551; 514/561; 514/575; 514/626

(58) Field of Classification Search ............ 514/6.1, 514/551, 561, 575, 626
See application file for complete search history.

(56) References Cited

U.S. PATENT DOCUMENTS 5,026,825 A  6/1991  Grebow
5,369,142 A  11/1994  Culbertson

OTHER PUBLICATIONS

Mingone C. J. et al., Protoporphyrin IX generation from δ-aminolevulinic acid elicits pulmonary artery relaxation and soluble guanylate cyclase activation, 2006, Am. J. Physiol. Lung Cell. Mol. Physiol. 291:L337-344.

Herman M.A., et al., Hemodynamic effects of 5-aminolevulinic acid humans, 1998, Journal of Photochemistry and Photobiology B: Biology, 43:61-65.

Nyamekye I. et al., Phtodynamic Therapy of Normal and Balloon-Injured Rat Carotid Arteries Using 5-Amino-Levulinic Acid, 1995, Circulation, 91:417-425.

Mingone C. J. et al., Protoporphyrin IX generation from δ-aminolevulinic acid elicits pulmonary artery relaxation and soluble guanylate cyclase activation, 2006,The FASEB Journal, 20:A400-d.

Search Report and Written Opinion for PCT/US07/007008, (2007).

*Primary Examiner* — Raymond Henley, III
(74) *Attorney, Agent, or Firm* — Nada Jain, P.C.

(57) ABSTRACT

The invention relates to methods of inducing smooth muscle relaxation, for example, a method of inducing relaxation of a vascular or a non-vascular muscle or a method of inducing relaxation of the microvasculature, in a subject in need thereof by promoting the accumulation of protoporphyrin IX in the smooth muscle.

18 Claims, 8 Drawing Sheets

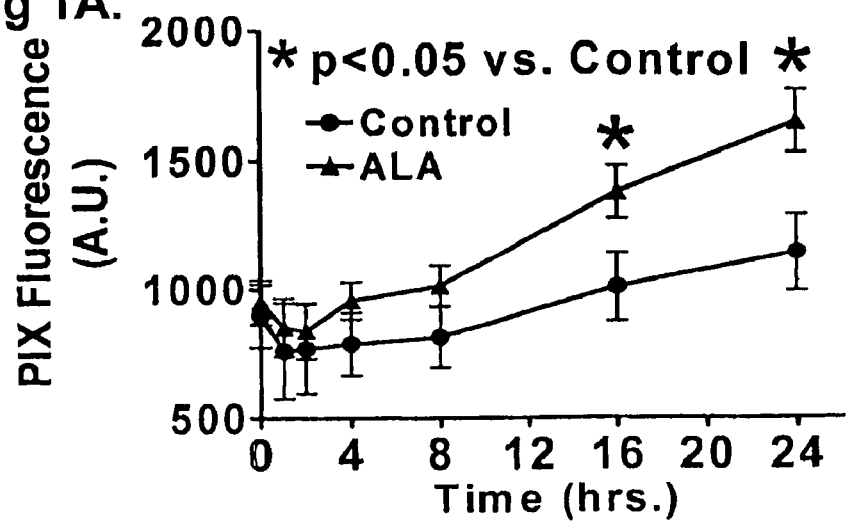
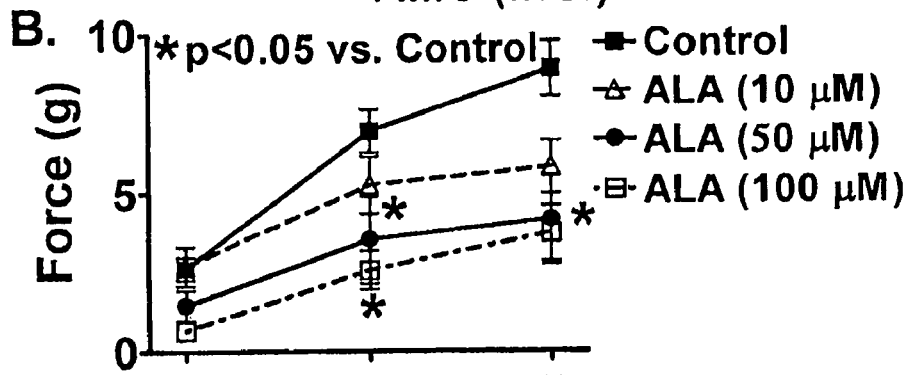
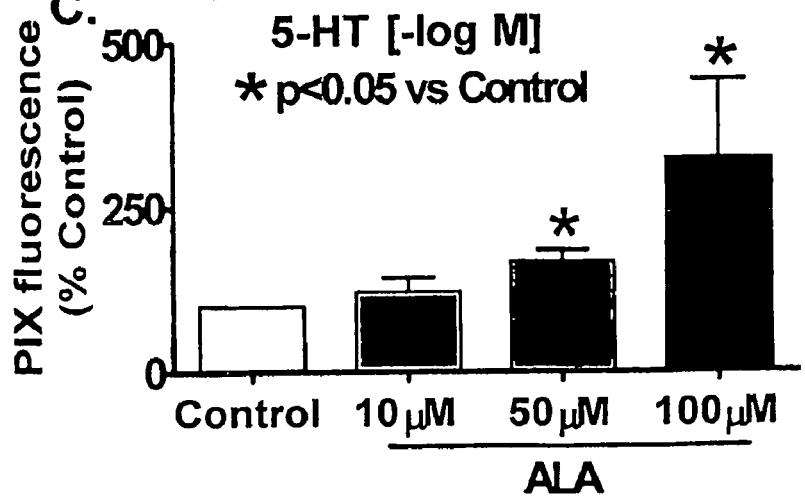
Fig 1A.

Fig 2A.
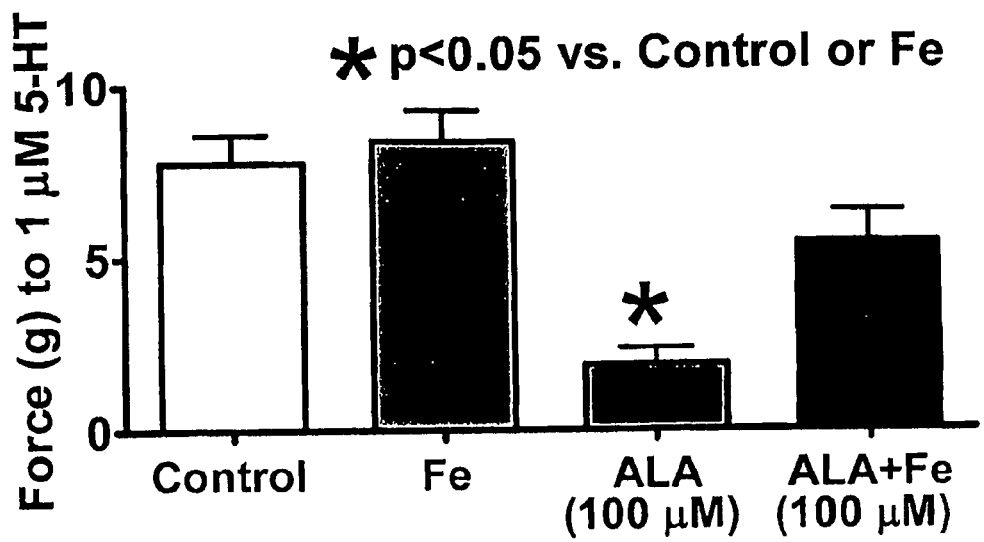
B.
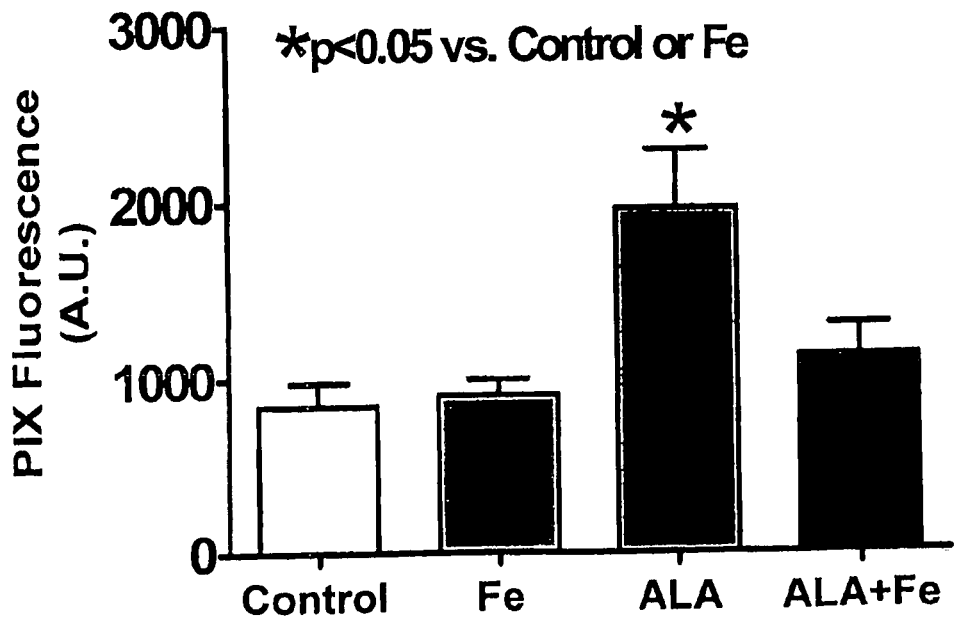

Fig 3A.
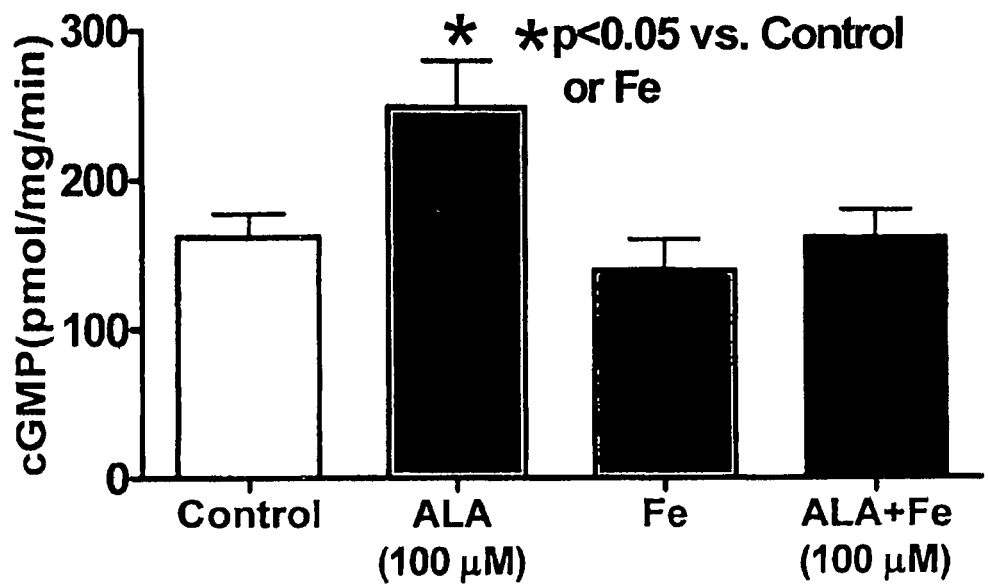
B.
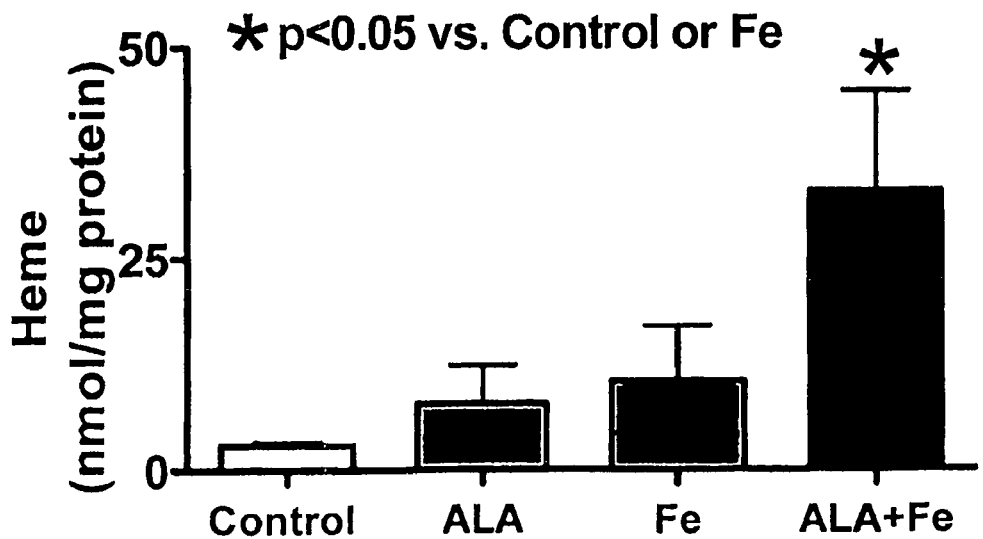

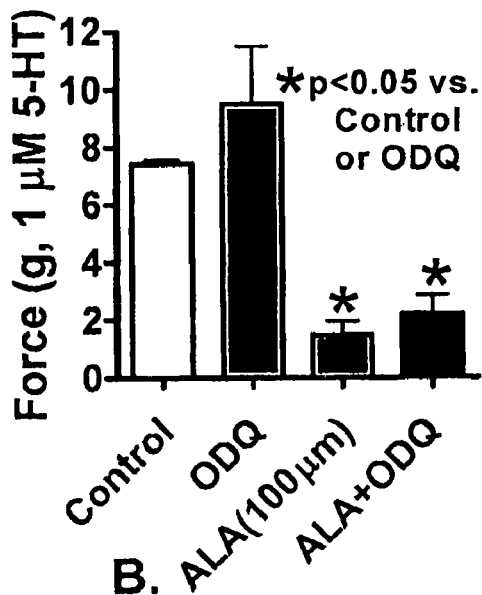
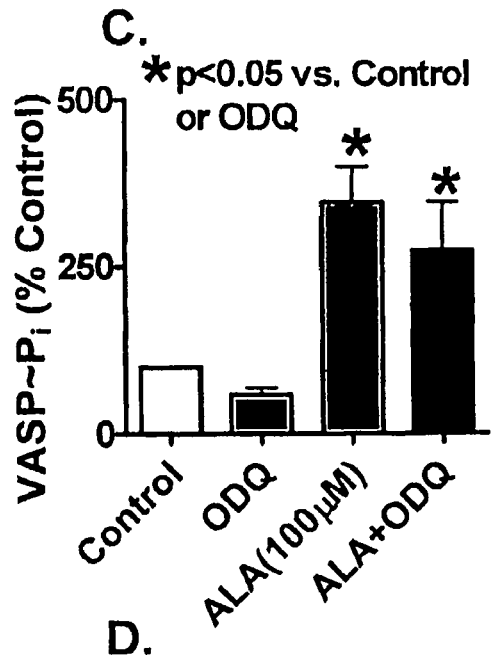
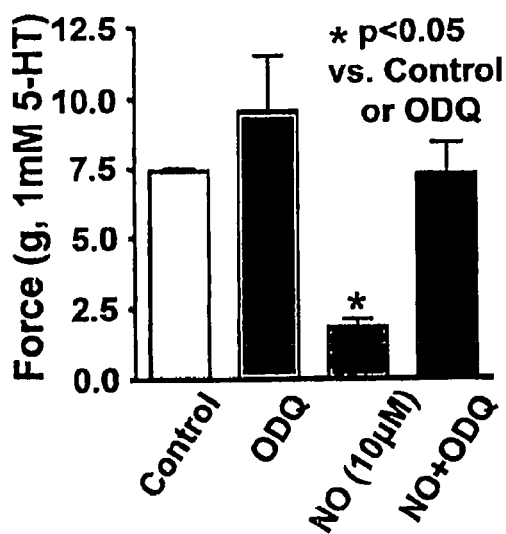
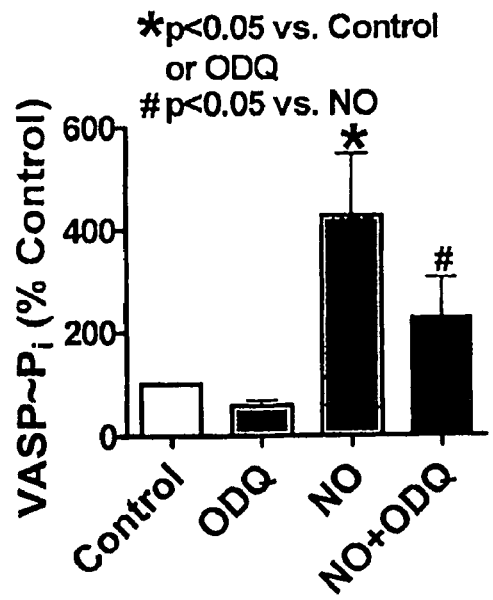
Fig 4A, B, C, D.

Fig 5A.
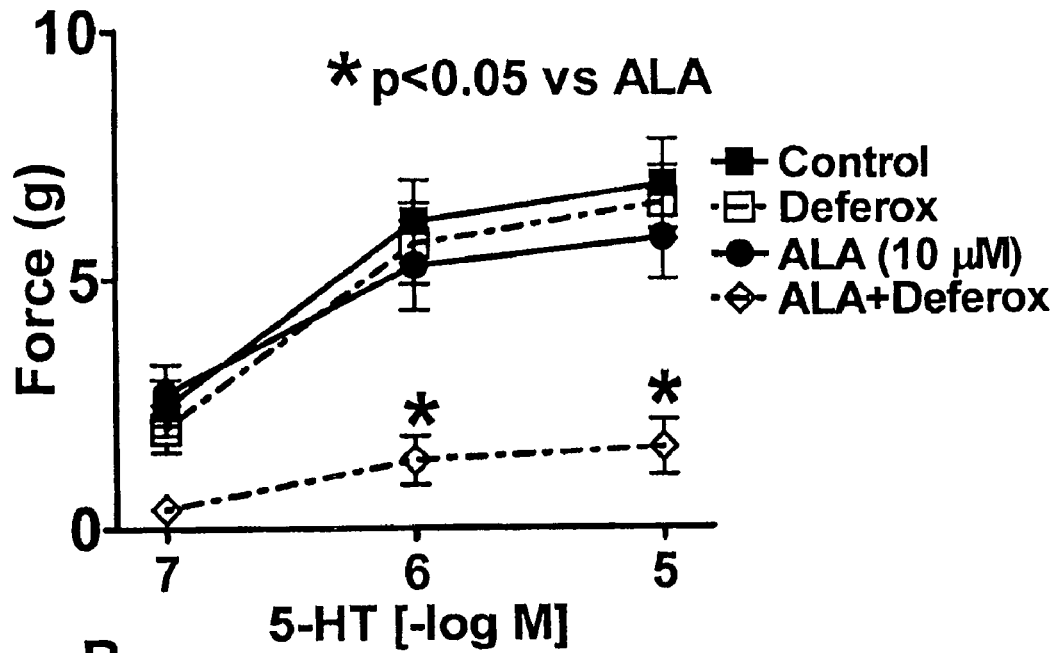
B.
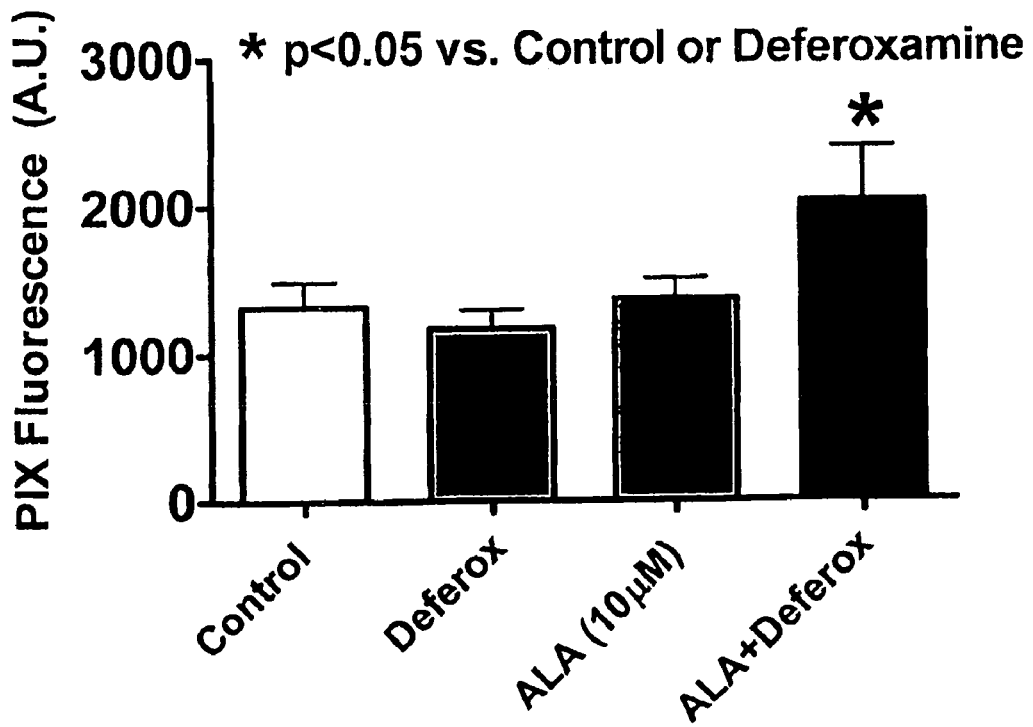

Fig 7A.
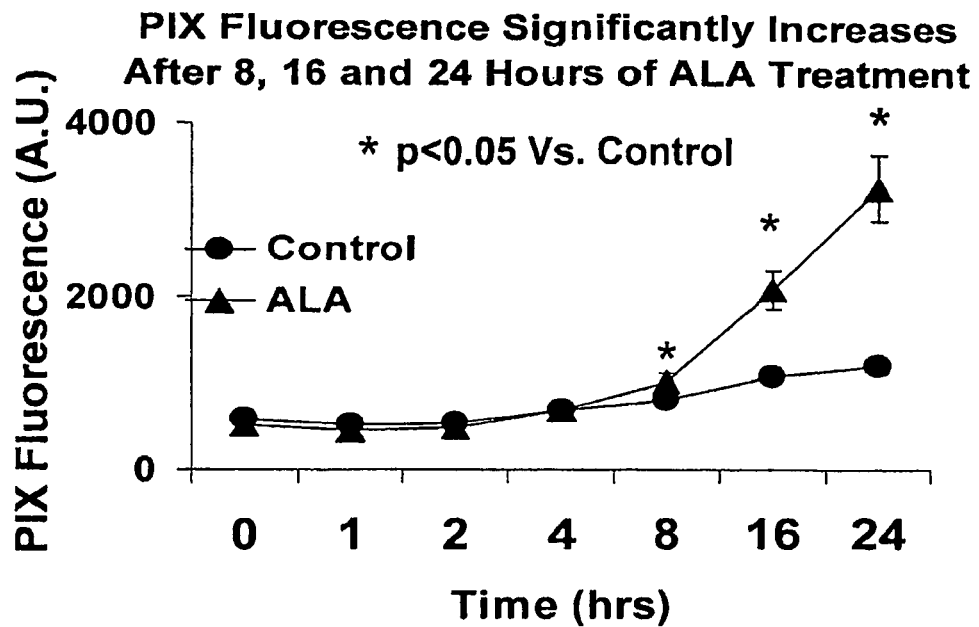
B
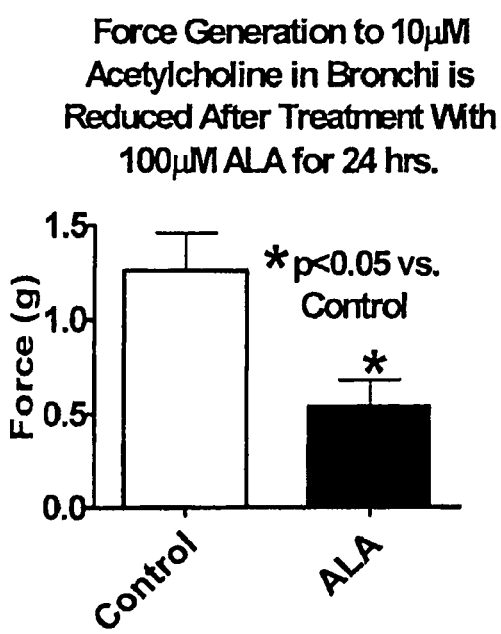
C
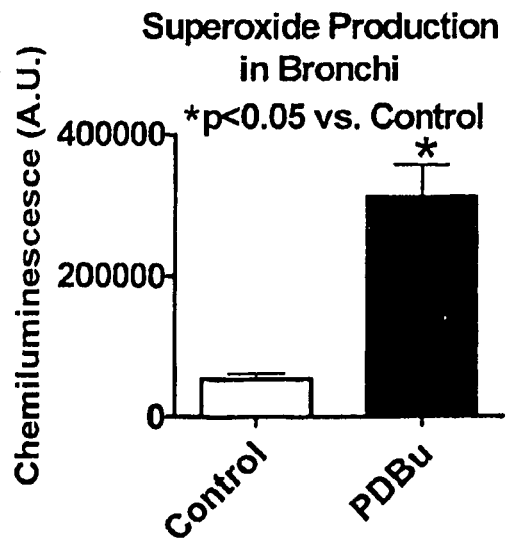

Fig 8 A.
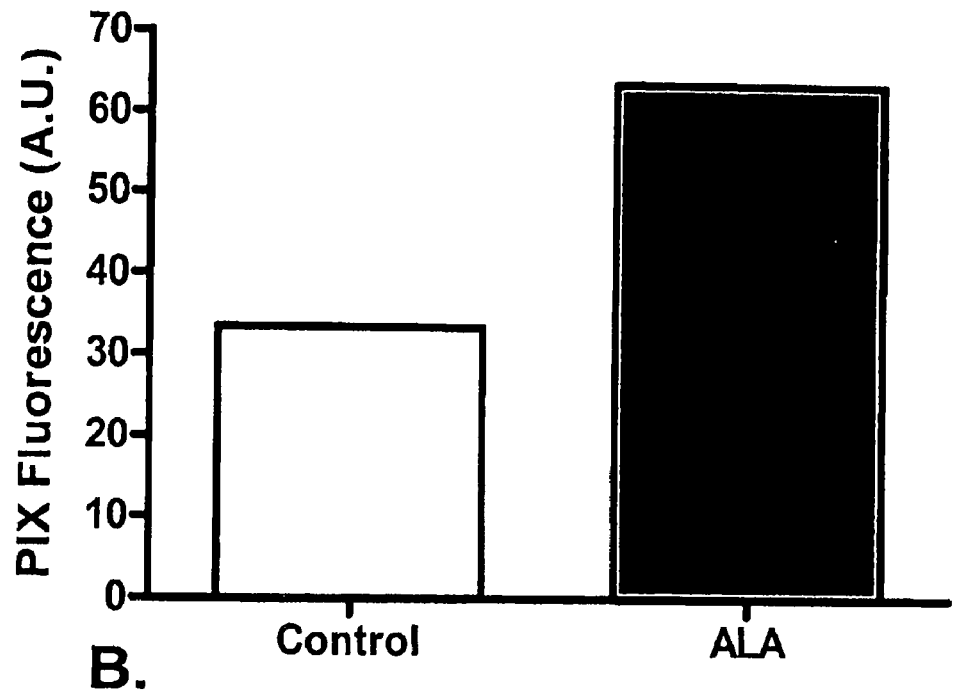
B.
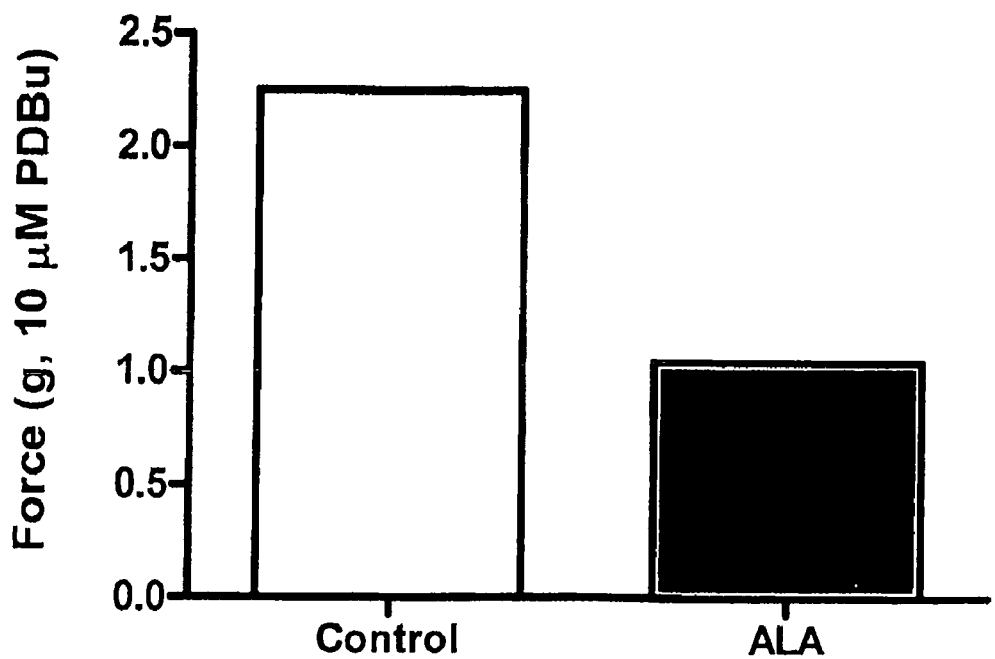

US 7,989,420 B2

SMOOTH MUSCLE RELAXATION

This application is a U.S. National Stage application of the International Application No. PCT/US2007/07008, filed Mar. 21, 2007, which claims priority from the U.S. provisional Appl. Ser. No. 60/786,369 filed Mar. 28, 2006, the disclosures of which are hereby incorporated herein by reference.

FIELD OF THE INVENTION

The invention relates to methods of inducing smooth muscle relaxation, for example, a method of inducing relaxation of a vascular or a non-vascular muscle or a method of inducing relaxation of the microvasculature, in a subject in need thereof by promoting the accumulation of protoporphyrin IX in the smooth muscle.

BACKGROUND

Processes controlled by cGMP function to coordinate relaxation of multiple forms of smooth muscle including vascular tissue and airways. While cGMP levels in tissues are regulated by its biosynthesis through membrane bound and cytosolic or soluble forms of guanylate cyclase and by its removal by phosphodiesterases, stimulation of cGMP production by activation of the sGC is generally the most dominant mechanism involved in physiological processes that initiate smooth muscle relaxation through cGMP. Nitric oxide (NO) is one of the best understood activators of sGC (2, 12, 23, 33), but there are many other mechanisms that appear to control the activity of sGC. For example, the ROS superoxide anion is formed as a result of multiple disease processes, and it prevents NO from stimulating sGC by converting it to peroxynitrate ($ONOO^-$). It also appears that superoxide, and oxidation of sGC thiols (25) and heme (11) sites prevent sGC activation by NO, and perhaps other stimuli. Asthma and most diseases altering the function of both vascular and non-vascular smooth muscle are known to be associated with increasing the activity of oxidases which are thought to produce reactive oxygen species (ROS) and reactive NO-derived species such as $ONOO^-$. Thus, increased oxidative stress in asthma and vascular diseases appear to impair cGMP-mediated bronchodilator and vasodilator mechanisms through the attenuation of mechanisms involved in sGC stimulation by NO and other processes. Since smooth muscle growth and inflammation are promoted by oxidant mechanisms and these mechanisms are inhibited by cGMP, alterations in these mechanisms may also contribute to the inflammation and remodeling that is seen in asthma, and vascular diseases, and other smooth muscle systems such as bladder dysfunction. The cGMP system is also thought to promote angiogenesis which will contribute to the restoration of tissue perfusion needed to treat complications of diabetes.

It was found that sGC purified from bovine lungs was stimulated by low nanomolar concentrations of the biosynthetic iron-free precursor of heme, protoporphyrin IX, in the process of elucidating how NO activates sGC (19, 34). However, it was not demonstrated that protoporphyrin IX could function as a regulator of sGC and relaxation in smooth muscle presumably because of the poor tissue permeability of this porphyrin molecule. The ability of protoporphyrin IX to stimulate sGC would not be impaired by oxidation of heme because it does not contain iron. In addition, the thiols that regulate sGC activation appear to be at a site that enhance NO binding to heme, and not at the actual heme/protoporphyrin IX binding site on sGC. Thus, if sGC activity in smooth muscle were activated by protoporphyrin IX, it might be resistant to inhibition by oxidant stress, and its mechanism could be developed as an approach to promote smooth muscle relaxation and other beneficial actions of cGMP under the oxidative stress-associated conditions present in asthma, vascular diseases and other disorders altering smooth muscle function.

NO activates sGC by binding a ferrous heme group, which appears to be a cofactor that is normally bound to sGC when it is isolated from tissues (6, 9, 34). Early studies investigating how NO activated sGC associated with the initial discovery that the iron-free biosynthetic precursor to heme, protoporphyrin IX activated sGC provided evidence for how sGC was activated (19). The protoporphyrin IX-activated form of sGC showed changes in enzyme kinetic properties (e.g. $K_M$ for Mg-GTP and maximum velocity) which resembled the NO-stimulated form of sGC (34). This observation resulted in the proposal that NO stimulated sGC by binding the iron of the heme of sGC resulting in a disruption of the bond normally present between an amino acid of sGC and the iron of the sGC heme (34). This amino acid was subsequently identified as a histidine residue (5, 31). Heme oxygenase-derived carbon monoxide has been reported to activate guanylate cyclase (4, 14) and causes vascular relaxation associated with increases in cGMP (14). Cleavage of the histidine bond to heme by NO distinguishes the marked stimulation of sGC activity by NO from a modest activation by CO (31), which does not result in the cleavage of the iron-histidine binding interaction (5). None of the other biosynthetic precursors of heme other than protoporphyrin IX made within mitochondria were found to alter sGC activity (19), and heme was observed to be a competitive inhibitor of the activation of sGC by protoporphyrin IX, suggesting both porphyrins bound to the same site on sGC (34). While drugs which mimicked human diseases of porphyrin metabolism associated with increased hepatic levels of protoporphyrin DC were observed to increase cGMP levels in liver (20), minimal work has been done to investigate the biological significance of this mechanism of regulating sGC, or if increasing cellular protoporphyrin IX levels could be used as a therapeutic approach. This may be because one would not expect protoporphyrin DC to be released from mitochondria in amounts that activate sGC, an enzyme known to be located in the cytosolic region of cells. Applicants have now unexpectedly found that protoporphyrin IX can be released from mitochondria in the amount sufficient to activate sGC.

The accumulation of protoporphyrin IX generated from the heme precursor δ-aminolevulinic acid (ALA) has been investigated as an approach to detect tumor cells based on its fluorescence and as a phototherapy. The scientific literature in this field documents that ALA is easily delivered to human patients and animals in amounts that promote detectable protoporphyrin IX accumulation. While measurements of protoporphyrin IX fluorescence in tumor and normal cells also detects fluorescence from its biosynthetic precursors uroporphyrin III and coproporphyrin III, the ratios of these porphyrins appears to be similar across a variety of cell types (27). Thus, tissue protoporphyrin IX fluorescence after treatment with ALA has been demonstrated in many studies to be closely associated with measurements of its levels in tissue extracts (30). The photosensitizing action of the protoporphyrin IX accumulated during exposure to ALA has also been developed as a phototherapy approach to kill tumors and other proliferating cells. A reduction in systemic and pulmonary artery pressure was reported as a factor which limited the doses of ALA that could be used in humans in this approach (13). However, the mechanism by which ALA directly or indirectly mediates these effects has not been elucidated. In addition, phototherapy using ALA administration to generate protoporphyrin IX has been investigated as an approach to treat restenosis through its cell death promoting actions (24, 28). Studies examining the treatment of animals with ALA for restenosis phototherapy have documented that ALA increases protoporphyrin IX fluorescence levels in the smooth muscle region of the arterial wall (21, 28). Treatment of isolated skeletal muscle arterioles with ALA has been used in studies on vascular regulation by the heme oxygenase system as a method of increasing heme availability for the production of carbon monoxide (22). However, there do not appear to be studies examining the regulation of sGC resulting from protoporphyrin IX generation by ALA in vascular tissue or any other cellular system.

SUMMARY OF THE INVENTION

The invention relates to methods of inducing smooth muscle relaxation by promoting the accumulation of protoporphyrin IX in the smooth muscle, and to the agents and compositions for use therein.

In one aspect, the invention relates to a method of inducing relaxation in a vascular smooth muscle.

In another aspect, the invention relates to a method of inducing relaxation in a non-vascular smooth muscle.

In yet another aspect, the invention relates to a method of inducing relaxation in the microvasculature.

In a further aspect, combination treatments described herein are also within the scope of the invention.

BRIEF DESCRIPTION OF THE DRAWINGS

FIG. 1A-C shows that ALA has a time-dependent effect on causing protoporphyrin IX accumulation and a prolonged relaxation of vascular smooth muscle. A) Time-dependent effects of organ culturing bovine pulmonary arteries (BPA) over 24 h in absence and presence of 100 µM ALA on protoporphyrin IX (PIX)-associated fluorescence detected by microplate analysis. Effects of culture for 24 h in the presence of different concentrations of ALA on B) the force generated upon exposure to 5-HT in the absence of ALA (n=8), and C) on the detection of PIX-associated fluorescence. Culture of BPA for 24 h in the presence of increasing concentrations of ALA showed significant increases in fluorescence at the 50 and 100 µM doses of ALA which significantly decrease force generation by serotonin (5-HT). Data in FIG. 1C are reported as the percent of the fluorescence seen in BPA organ cultured in the absence of ALA for the comparison of different experimental groups. (n=11, 12 and 8 for 10, 50 and 100 µM ALA, respectively).

FIG. 2A-B shows that iron functions as an inhibitor of ALA-elicited relaxation associated with its effect on decreasing protoporphyrin IX. Effects of organ culture with combinations of 100 µM ALA and 100 µM Fe on BPA (A) force generation by 5-HT and (B) protoporphyrin IX (PIX)-associated fluorescence. The decreased level of force generation in ALA treated vessels was improved in the presence of Fe, whereas the ALA-elicited increase in fluorescence associated with protoporphyrin IX detection was attenuated by Fe. (n=5-8, $p<0.05$ vs. Control).

FIG. 3A-B shows that ALA elicits an increase in sGC activity which is regulated by the availability of iron, due to iron promoting an increase in conversion of protoporphyrin IX to heme. Effects of organ culture with combinations of 100 µM ALA and 100 µM Fe on BPA (A) sGC activity and (B) heme content. ALA increased sGC activity under conditions where elevated levels of protoporphyrin IX-associated fluorescence was detected. Fe treatment with ALA increased heme and prevented the increase in sGC activity. (n=7, $p<0.05$).

FIG. 4A-D shows that the sGC heme oxidant ODQ attenuates the actions of nitric oxide, but does not inhibit the actions of ALA, on cGMP-mediated protein kinase regulation and relaxation of BPA. The effects of (A,C) organ culture with 100 µM ALA or (B,D) relaxation of organ cultured BPA by 10 µM of the nitric oxide donor spermine-NONOate and 10 µM ODQ on (A,B) force generation to 5-HT and (C,D) VASP serine-239 phosphorylation associated with cGMP-dependent protein kinase activation. The sGC heme oxidant inhibitor, ODQ, did not significantly alter the decreased levels of 5-HT contraction seen in BPA exposed to ALA (n=6). ALA and spermine-NONOate (NO) increased VASP phosphorylation in a similar manner, however, only NO-induced VASP-phosphorylation is decreased in the presence of ODQ (n=5, $p<0.05$). Data is normalized to total VASP. While ODQ appeared to decrease VASP phosphorylation, and NO appeared to increase VASP phosphorylation in the presence of ODQ, these changes did not reach statistical significance.

FIG. 5A-B shows that removal of iron enhances the action of ALA on ALA-elicited relaxation and protoporphyrin IX fluorescence. Effects of organ culture with a low dose of ALA (10 µM) on BPA (A) force generation by 5-HT and (B) protoporphyrin IX (PIX)-associated fluorescence. The low dose of ALA did not significantly alter force generation or PDC-associated fluorescence. The iron chelator deferoxamine (100 µM) attenuated force generation and increased PIX-associated fluorescence in the presence of the low dose of ALA compared to the Control and ALA-treated BPA ($p<0.05$, n=8-12).

FIG. 7A-C shows that ALA has a time-dependent effect on causing protoporphyrin IX accumulation and a prolonged relaxation of airway smooth muscle. Organ culture of bovine bronchi (~3 mm diameter) with 0.1 mM ALA caused a time-dependent increase in protoporphyrin IX fluorescence (FIG. A) and decreased force generation to 10 µM acetylcholine (ACh) compared to airways organ cultured for 24 hrs in the absence of ALA (Fig. B). Fig. C shows that exposure of bovine airways the protein kinase C activator 10 µM phorbol ester dibutyrate (PDBu) for 30 minutes causes an increase in superoxide detected by 5 µM lucigenin chemiluminescence.

FIG. 8A-B demonstrates that ALA can be used in vivo to promote a prolonged relaxation which is resistant to oxidant conditions. The data shown in the figures provide evidence that a single i.p injection of 60 mg/kg of ALA causes increases in protoporphyrin IX fluorescence in endothelium-rubbed aorta compared to aorta from saline-injected control rats 24 hours after the treatment of the animals. Aorta from these animals show a decreased contraction to the protein kinase C activator 10 µM phorbol 11,12-dibutyrate (PDBu), a contractile agent that increases superoxide in multiple smooth muscle preparations, including the airway smooth muscle shown in FIG. 7C.

DETAILED DESCRIPTION OF THE INVENTION

Figure 6:
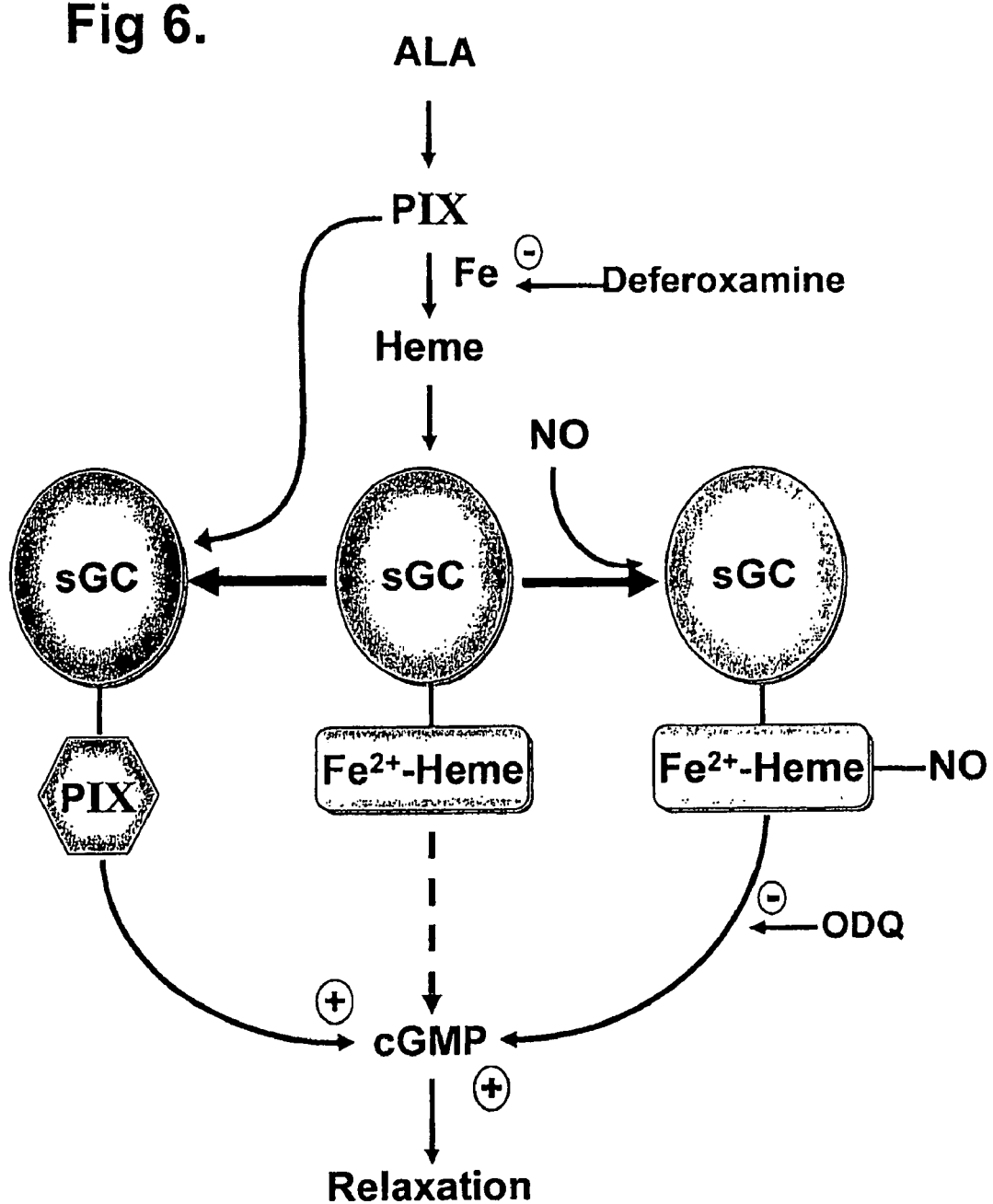
FIG. 6 represents a model showing how ALA promotes the biosynthesis of protoporphyrin IX (PIX) in a manner controlled by the availability of Fe, and how protoporphyrin IX increases cGMP production and smooth muscle relaxation through binding the heme site of sGC. Since ODQ is an oxidant of the heme of sGC, it attenuates increases in cGMP and relaxation caused by NO but, not responses caused by protoporphyrin IX.

All references cited herein are hereby incorporated herein by reference, in case of any inconsistency the instant disclose governs.

The invention relates to a method of inducing smooth muscle relaxation, for example, a method of inducing relaxation of a vascular or a non-vascular muscle or a method of inducing relaxation of the microvasculature, in a subject in need thereof by promoting the accumulation of protoporphyrin IX in the smooth muscle. In certain embodiments, the accumulation of protoporphyrin IX is achieved by administering to the subject in need thereof an agent that directly promotes an increase of protoporphyrin IX in the smooth muscle, for example, by administering an effective amount of the δ-aminolevulinic acid (ALA), and/or an ester, amide, a pharmaceutically acceptable salt and/or a metabolic precursor thereof. In other embodiments, the accumulation of protoporphyrin IX is achieved by administering to the subject in need thereof an agent that indirectly promotes an increase of protoporphyrin IX in the smooth muscle, for example, by administering an agent that preserves the endogenous levels of protoporphyrin IX, for example, by depleting available iron and decreasing ferrochelatase activity. In other embodiments, the above methods are practiced in combination. Agents known to promote increased smooth muscle relaxation by stimulating soluble guanylate cyclase (sGC) and/or by inhibiting cGMP removal by phosphodiesterases may also be used.

As used herein, the phrase "smooth muscle relaxation" includes inhibiting smooth muscle contraction (e.g. vasospasm), improving contractile dysfunction (e.g. of pulmonary and systemic vasculature), improving blood flow (e.g. in the microvasculature), improving organ perfusion and/or tissue oxygen delivery. The phrase "directly promoting the accumulation of protoporphyrin IX" means increasing and/or inducing the biosynthesis of protoporphyrin IX using its precursor such as ALA. The phrase "indirectly promoting the accumulation of protoporphyrin IX" refers to increasing and/or preserving the levels of protoporphyrin IX other than via its precursors, such as by preserving protoporphyrin IX from metabolism (e.g. cellular conversion to heme by ferrochelatase) and/or delivering protoporphyrin IX to the smooth muscle. Methods for measuring protoporphyrin IX will be apparent to those of skill in the art.

The methods described herein are effective in promoting prolonged relaxation in both vascular and non-vascular smooth muscle. As used herein, the phrase "prolonged relaxation" means a prolonged action resulting in increased smooth muscle length, dilation and/or decreased force generation, and/or rates of contraction by smooth muscle, and/or elimination of spastic contractile function. For example, relaxation may be maintained for at least six (6) hours, for example, for at least 12 or 24 hours.

The advantage of the present methods is that they are effective (unlike certain therapies known to date) under the oxidant stress conditions, which are often associated with disease processes in a mammal, e.g. a human or a veterinary animal (e.g. a dog, a horse or a cat). Thus, relaxation of smooth muscle according to the present invention is advantageous in treating conditions recited herein, for example, the increased contraction of smooth muscle that contributes to many diseases and/or conditions.

In view of the disclosure herein, a person of skill in the art can envision the subjects (mammal, e.g. human or a veterinary animal) as well as diseases and/or conditions that benefit from the methods described herein. For example, a subject suffering from: a disease and/or condition associated with contractile dysfunction of smooth muscle (e.g. pulmonary and systemic vascular, airway and other forms of smooth muscle); a disease and/or a condition characterized by an impaired microvascular blood flow (e.g. in a diabetic patient); an impaired lung function such as airway hyperreactivity, obstruction and/or asthma; a disease affecting the circulatory system, blood flow (e.g. microvascular blood flow) or cardiac function such as coronary artery disease, diabetes (e.g. vascular complication of diabetes such as impaired microvascular blood flow in diabetes), atherosclerosis, stroke, renal dysfunction, erectile dysfunction or female sexual dysfunction, complications of pregnancy including impaired uterine-placental function, multiple forms of hypertension, including pulmonary hypertension or hypertension of any other organ, heart failure; diseases affecting the digestive system and urinary tract including urinary urge and/or incontinence, bladder conditions, intestinal smooth muscle hyperreactivity, choledocholithiasis or cholelithiasis, urolithiasis; and other conditions influenced by blood flow such as exercise and aging. A person of skill in the art will appreciate, in view of the disclosure herein, that certain prophylactic treatments are also within the scope of the invention, e.g. administration of agents described herein prior to surgery.

The invention relates to relaxing smooth muscle in vivo or ex vivo with a therapeutically effective amount of the agents described herein, for example, delta-aminolevulinic acid (ALA), an ester, amide, a pharmaceutically acceptable salt and/or a metabolic precursor thereof. A person of skill in the art would know how to prepare appropriate dosage forms (e.g. depending on the mode of administration) and select pharmaceutically acceptable carrier(s) for use therein using the guidance provided herein and the general knowledge in the art.

The agents for use in the present invention, e.g. ALA, may be administered orally, by inhalation, nasally, by injection (e.g. intravenously), aerosolized, topically, by implantation, as a suppository, intracoronary, or other known methods of drug delivery.

With respect to the use of ALA, also within the scope of the invention are embodiments using modified forms of ALA such as those designed to transport the ALA, or forms that are metabolized in the body of a mammal in a manner which releases ALA, and/or using a known method of increasing ALA biosynthesis. Examples of methods to increase ALA biosynthesis include promoting the depletion of cellular heme by increasing heme oxygenase activity, and using any form of tissue protein delivery, or the art of transfection methods to increase the expression of ALA synthase.

Using guidance in the specification and general knowledge in the art, a person of skill in the art can optimize the effective amount of the agents for use in the invention, depending on known factors such as disease or condition, mode of delivery, weight of a subject etc. For example, ALA may be administered from about 1 to about 100 mg/kg, or doses of ALA which expose target tissues to about 1 to about 100 µM ALA for a period of time determined by therapeutic efficacy. A person of skill in the art can select known methods for determining or testing the effects of the therapy.

In certain embodiments, the ALA therapy (inclusive of any ALA form administered) can be used in combination with additional treatments to increase its efficacy, for example, method available to those skilled in the art that are known to bind or chelate iron, promote the accumulation of protoporphyrin IX and/or deplete cellular heme.

Methods for binding iron include, for example, the use of iron binding agents (e.g. deferoxamine) or tissue permeable forms of an iron binding proteins, or therapeutic treatments (e.g. tissue specific transfection methods) known in the art of increasing the expression of iron binding proteins (e.g. ferritin).

Methods for promoting the accumulation of protoporphyrin IX include, for example, methods of depleting iron, methods of administering a modified form of protoporphyrin DC which is tissue permeable or metabolized to generate protoporphyrin IX, and any known therapeutic method of inhibiting or decreasing the expression of ferrochelatase, including any methods in the art of transfection (e.g. shRNA or siRNA) which would decrease its expression.

Methods of heme depletion include, for example, heme oxidation by exposure of smooth muscle in vitro or in vivo to any known heme oxidant, such as 1-10 μM 1H-[1,2,4]oxadiazolo[4,3-α]quinoxalin-1-one (ODQ) or methylene blue, alone or in combination with any known method of increasing the activity or expression of heme oxygenase.

An alternative smooth muscle relaxing therapy is the use of treatments for heme depletion in combination with treatments for promoting protoporphyrin IX accumulation or with therapeutic drugs designed to activate sGC by binding the protoporphyrin IX binding site on sGC.

The methods described herein can also be used in combination with any approach employed in the art of therapeutic treatment of smooth muscle dysfunction based on increasing the activity of sGC and/or regulation by cGMP. This includes therapies that increase the expression and/or activity of sGC (or other known forms of guanylate cyclase), prevent the removal of cGMP by inhibiting the activity or decreasing the expression of phosphodiesterases enzymes and/or molecular approaches that increase the beneficial effects of cGMP on smooth muscle function.

In certain embodiments, ALA (and other forms described herein) is delivered in a therapeutically effective dose to the airways of lungs affected by asthma by aerosol in the absence or presence of an orally active iron binding agent such as deferoxamine to prevent an anticipated asthmatic attack or suppresses asthma for prolonged periods of time. An alternative example would be to treat the impairment of microvascular blood flow in diabetes, which leads to amputation, with a topical form that delivers it in a therapeutically effective dose for increasing blood flow in the absence or presence of an orally active iron binding agent such as deferoxamine. The topically treated area would preferably be protected from light to prevent the increased photosensitivity caused by the accumulation of protoporphyrin IX.

The effects of the methods described herein in humans or animals would be readily observed in the relief of symptoms associated with the disease such as reduced difficulty in breathing, decreased angina, increased blood flow, cardiac function or exercise tolerance, prevention of a subsequent heart attack or stroke, improved fetal oxygenation, improved bladder control and decreased urinary urge, reduced intestinal discomfort, improved sexual function, improved success in surgery, organ transplant, etc.

The invention is further described in the following non-limiting examples.

EXAMPLES

Example 1

Experimental Procedures

Materials: Spermine-NONOate, ODQ and cGMP Enzyme Immunoassay (ELISA) kits were purchased from Cayman Chemical. Anti-VASP, phospho (Ser239) and Anti-VASP antibodies were obtained from Cell Signaling, and anti β-sGC subunit antibodies was obtained from Sigma. Heme was measured using a QuantiChrom heme assay kit purchased from BioAssay Systems. All gasses were purchased from Tech Air (White Plains, N.Y.). All salts used were Analyzed Reagent Grade from Baker Chemical Company and all other chemicals were obtained from Sigma Chemical Company.

Organoid Culture Isolated Arteries for Heme Modulation. Intralobar BPA were isolated from slaughterhouse-derived bovine calf lungs, cleaned from surrounding tissue, and placed in 37° C. Dulbecco's Modified Eagle Medium (DMEM) containing 10% fetal bovine serum, penicillin, streptomycin, and fungizone (complete media). The arteries were isolated and cut into rings ~2 mm in diameter and width, and the endothelium was removed by gentle rubbing of the lumen. Various compounds (i.e. ALA, $FeSO_4$(Fe), deferoxamine) were added as described in the Results to various experimental groups, and these arteries were organ cultured overnight for 24 h in complete media in a 37° C.-5% $CO_2$ incubator. Preliminary experiments on the time course for detection protoporphyrin IX accumulation and the effects of organ culture with doses of ALA in the 10-100 μM concentration range on contractile function, and minimizing the duration of organ culture were considerations that contributed to selecting the 24 h culture period used in this study.

Studies on the Regulation of Contractile Function. Following the overnight incubation, arterial rings were mounted on wire hooks attached to Grass (FT03) force displacement transducers for measurement of changes in isometric force. Tension was adjusted to 5 g, which is the optimal passive force for maximal contraction. Changes in force were recorded on a Grass polygraph (model 7), while vessels were incubated in 10-ml baths (Metro Scientific), which were individually thermostated (37° C.) in Krebs buffer gassed with 21% $O_2$-5% $CO_2$ (balance $N_2$) in the absence of compounds used to modulate BPA protoporphyrin IX levels. Arteries were incubated for 1 h during which passive tension was adjusted to maintain 5 grams. The vessels were then depolarized with Krebs containing 123 mM KCl (High $K^+$) in place of NaCl, followed by re-equilibration with Krebs, prior to exposure to the experimental protocols. Following the wash with Krebs buffer after the High $K^+$ treatment, and a 30 min equilibration, BPA were then contracted with serotonin (5-HT) in a dose dependent manner to determine the response to this contractile agent. In some experiments, BPA were pretreated with the sGC inhibitor, 10 μM ODQ, for 15 min before contraction with serotonin. The effects of ODQ on relaxation to NO was determined by first contracting organ cultured control and ODQ-treated BPA with 1 μM 5-HT (after the initial exposure to increasing concentrations of 5-HT and a 30 min equilibration in Krebs).

Determination Changes in Protoporphyrin 1x and Heme Levels. Methods for the detection of protoporphyrin IX tissue fluorescence developed for the detection in cancerous cells with tissue depths of up to several millimeters (27) were adapted for detecting changes in the endogenous levels of protoporphyrin IX in BPA rings which were organ cultured with ALA. When excited with light in the regions of 505 and 540 nm, protoporphyrin IX has an emission in the region of 635 nm. Studies measuring the ALA-elicited accumulation of protoporphyrin IX in tissues developed for the detection of cancerous cells have consistently found that the observed increase in fluorescence emission at 635 nm was closely associated with the accumulation of protoporphyrin IX in the tissue studied (30). Increases in protoporphyrin IX were measured using an excitation wavelength of 528±20 nm and emission of 620±40 nm in intact vessels. Ring segments of approximately equal size (~4 mm in diameter and length) were centered on the bottom of the ~6 mm diameter wells of a 96 well microplate with 200 μl of Krebs containing with 10 mM Hepes buffer (pH 7.4), and the fluorescence was measured from the bottom surface of the plate using BIOTEK fluorescent microplate reader (Model FLx800i). Data are reported in the arbitrary fluorescence units measured (AU), after subtraction of the low levels of background fluorescence observed in the absence of BPA.

Heme was quantified in BPA homogenates using a QuantiChrom heme assay kit purchased from BioAssay Systems, and changes in absorbance were measured in a BIOTEK scanning microplate spectrophotometer. Briefly, segments were homogenized in 20 mM MOPS+sucrose buffer and diluted to approximately 5 mg protein/ml. Homogenates were centrifuged at 2000×g for 5 min, and 50 µl of supernatant obtained were assayed for their heme content based on the manufacture's instructions, employing measurements of changes in absorbance at 400 nm. The protein content of the supernatant was measured with Biorad protein assay kit, and tissue heme levels were reported as nanomoles/mg protein.

Western Blot Analysis of Phosphorylated VASP and sGC Expression

Rings from studies on contractile function were snap-frozen in liquid nitrogen, crushed and homogenized in lysis buffer (50 mM Tris-HCl, pH 8.0, 150 mM NaCl, 1 mM EDTA, 1% Triton X-100, 0.5% sodium deoxycholate, 0.1% sodium dodecyl sulfate, 1% of a protease inhibitor cocktail (Sigma) and 1% of a phosphatase inhibitor cocktail (Sigma). The protease inhibitor cocktail included 4-(2-aminoethyl) benzenesulfonyl floride hydrocholride, aprotinin, bestatin hydrochloride, N-(trans-epoxsuccinyl)-L-leucine-4-guanidinobutylamide, leupeptine hemisulfate, pepstatin and the phosphatase inhibitor cocktail included sodium orthovandate, sodium molybdate, sodium tartarate, and imidazole. Protein concentration was determined and 30 µg of protein samples were prepared in electrophoresis sample buffer containing 3% SDS and 3% β-mercaptoethanol and were separated using a 12% gel SDS-PAGE electrophoresis. Membranes were blocked for 1 h in TBST-5% milk and incubated overnight with phospho-VASP antibodies (diluted 1:1000). Membranes were exposed to a secondary horse radish peroxidase linked antibody and visualized with an ECL kit (Amersham). The membranes were subsequently exposed to X-OMAT autoradiography paper (Kodak). Membranes were stripped with TRIS-HCl buffer with 100 mM β-mercaptoethanol at 50° C. for 30 min. Membranes were subsequently washed, blocked and detected for total VASP. Each measurement of phosphorylated VASP was normalized to the total level of VASP, and data are reported as the percent of the levels of phosphorylated VASP seen in control arteries not exposed to agents which modulate the activity of sGC. Expression of sGC was detected with β-sGC subunit antibodies (diluted 1:2000), employing anti-rabbit secondary antibodies, and a protocol where membranes were blocked for 2 h. After analyzing for sGC protein expression, blots were stripped and re-probed for the detection of α-actin protein levels, which were used for normalization of data for statistical analysis based on protein loading.

Assay of sGC Activity in BPA Homogenates

Guanylate cyclase activity of homogenates of BPA was measured by enzyme immunoassay of the amounts of cGMP generated. Briefly, BPA were pulverized in liquid nitrogen and homogenized in MOPS buffer 1:3 wt to buffer ratio at 5° C. Reaction mixture (0.2 ml final volume) contained 20 mM MOPS-KOH (pH 7.4), 0.1 mM GTP, 2 mM $MgCl_2$, 0.3 mM of the phosphodiesterase inhibitor 3-Isobutyl-1-methylxanthine, a GTP-regenerating system consisting of 10 mM phosphocreatine and 150 U/ml creatine phosphokinase, and 0.1 ml of homogenate (11, 15), and test agents, as indicated. Assays of sGC activity were initiated by the addition of BPA homogenate. Incubations were conducted for 10 min at 37° C., and they were terminated by the addition of 0.1 ml of preheated 12 mM EDTA. This was followed by boiling the assay mixtures for 10 min and a subsequent addition of 5% trichloroacetic acid. The precipitate was removed by centrifugation and the supernatant was washed three times with water-saturated diethyl ether. Residual ether was removed by incubation at 70° C. for 5 minutes, prior to measurement of cGMP by ELISA (Cayman), as described in the manual supplied by manufacturer of the ELISA kit.

Statistical Analysis

Data are reported as mean±SEM with n describing the number of BPA from different animals. Statistical analyses were performed by using a one-way ANOVA with a post hoc Bonferroni correction for comparison between multiple groups.

Results

Effect of ALA on Vascular Contraction to 5-HT and Detection of Protoporphyrin IX Organ culture of BPA with 100 µM ALA was observed to increase in tissue fluorescence potentially originating from protoporphyrin IX after 16 and 24 h of incubation (See FIG. 1A). When examined after 24 h of organ culture in studies examining contractile function to 0.1-10 µM 5-HT in the absence of ALA, exposure to 100 µM ALA was observed markedly inhibit force generation to doses of 5-HT that induce submaximal contraction (FIG. 1B). The data in FIG. 1B show that the organ cultured Control BPA contracted to 5-HT, and organ culture with the 10 µM dose of ALA appeared to depress force generation at higher doses of 5-HT. However, these changes did not reach statistical significance. Statistically significant decreases in force generation to 5-HT in the range of 50-90% were observed in the presence of the 50 µM and 100 µM doses of ALA. As shown in FIG. 1C, the 10 µM dose of ALA did not cause a detectable increase in fluorescence potentially originating from protoporphyrin IX in intact vessels, whereas, 50 µM and 100 µM ALA caused increases in fluorescence of up to 2-fold greater than the background fluorescence of BPA. The increase in BPA fluorescence caused by 100 µM ALA was similar to the fluorescence produced by a 3 µM solution of protoporphyrin IX under the conditions examined. These data are consistent with organ culture with 50-100 µM ALA resulting in increases in levels of protoporphyrin IX detected by fluorescence associated with decreased in force generation when exposed to 5-HT.

Effect of Fe on Inhibition of Vascular Reactivity and Increased Protoporphyrin IX-Associated Fluorescence Caused by ALA Since the availability of Fe may influence protoporphyrin IX levels by serving as a cofactor for its conversion to heme, the influence of the presence of 100 µM Fe during organ culture was examined. As shown in FIG. 2A, the presence of organ culture with Fe did not alter force generation by 5-HT. However, Fe reversed the force attenuating effects of organ culture with 100 µM ALA. Data in FIG. 2B show that organ culture with Fe did not alter the background fluorescence of BPA, however, it reversed the increase in protoporphyrin IX fluorescence seen in the presence of 100 µM ALA. These data are consistent with Fe lowering the levels of protoporphyrin IX in BPA associated removing its force depressing or relaxing effects on the contraction to 5-HT.

Influence of Organ Culture in the Absence and Presence of ALA and Fe on BPA sGC Activity and Heme Levels The enzyme activity of sGC in BPA was examined to detect if organ culture in the absence and presence of combinations of 100 µM ALA and Fe influenced sGC activity. As shown in FIG. 3A, an increase in BPA homogenate sGC activity was seen in the presence of ALA, and organ culture with Fe alone or ALA+Fe did not alter sGC activity, suggesting that Fe was reversing the effects of ALA on sGC activity. Changes in the expression of sGC did not appear to be the cause of increased sGC activity because based on Western analysis, BPA organ cultured with 100 μM ALA had 71±19% (n=4) of the levels of sGC detected in BPA organ cultured in the absence of ALA. The levels of heme were measured in the absence and presence of combinations of 100 μM ALA and Fe to determine influence of these conditions on heme biosynthesis. The data in FIG. 3B show that while Fe or ALA alone appeared to increase BPA heme levels under the conditions examined, the changes in heme did not reach statistical significance. However, organ culture with 100 μM ALA+Fe resulted in a marked increase in heme, which was statistically significant. These data are consistent with sGC activity being stimulated under conditions where an elevated level of protoporphyrin IX was detected (100 μM ALA), and that elevated levels of heme (100 μM ALA+Fe) did not appear to influence basal sGC activity.

Influence of the sGC Heme Oxidant ODQ on Decreases in BPA Force Generation Resulting from Organ Culture with ALA The actions of ODQ, an oxidant of the ferrous form of the heme of sGC which inhibits of sGC activation by NO and carbon monoxide (CO) (8, 29), on the decrease in force elicited by organ culture of BPA in the presence of ALA was examined to characterize the role of heme-binding dependent mechanisms of sGC activation in decrease it force that was observed under these conditions. The data in FIG. 4A show that 10 μM ODQ did not alter force generation to 5-HT or the decrease in contraction to 5-HT observed in the presence of 100 μM ALA. Organ cultured BPA relaxed to the NO donor 10 μM spermine-NONOate (See FIG. 4B), and pretreatment with 10 μM ODQ markedly attenuated relaxation to this NO donor. Thus, the depression of force observed in BPA organ cultured with ALA does not appear to be mediated through a mechanism dependent of the ferrous heme form of sGC.

Organ Culture of BPA with ALA Increases the cGMP-Associated Phosphorylation of VASP Increases in the phosphorylation of serine-239 on VASP in BPA organ cultured in the absence and presence of 100 μM ALA was examined as an indicator of cGMP-dependent protein kinase activation. BPA organ cultured with 100 μM ALA showed an increase in VASP phosphorylation (See FIG. 4C), which was similar in magnitude to the increase caused during relaxation of organ cultured BPA when they were exposed to a 10 μM dose of the NO donor spermine-NONOate (FIG. 4D). As shown in FIG. 4, the heme oxidant inhibitor of sGC ODQ did not significantly alter the increase in serine-239 VASP phosphorylation caused by organ culture with ALA under conditions where it was observed to attenuate the increase caused by the NO donor. Thus, organ culture with 100 μM ALA appears to be promoting increases in VASP phosphorylation associated with cGMP-dependent protein kinase activation in a manner similar to 10 μM spermine-NONOate, however, this effect of ALA does not appear to be dependent on sGC being stimulated through a ferrous heme-dependent mechanism.

Effect of the Iron Chelator Deferoxamine on Vascular Contraction and Protoporphyrin IX Detection Resulting from Organ Culture of BPA with a Low Dose of ALA Force generation to 5-HT and increases in the detection of protoporphyrin IX fluorescence were not significantly altered by the low dose of ALA (10 μM) examined in FIG. 1. Thus, the effect of organ culture with the iron chelator deferoxamine was examined to determination if decreasing the availability of iron enhanced protoporphyrin IX levels and its effects on decreasing force. As shown by the data in FIG. 5A, organ culture with 100 μM deferoxamine did not alter contraction to 5-HT, but the presence of this iron binding agent during organ culture markedly reduced the contraction to 5-HT in the presence of 10 μM ALA. Organ culture with the iron chelator deferoxamine did not alter the basal levels of protoporphyrin IX-associated fluorescence. However, as shown in FIG. 5B, organ culture with 10 μM ALA in the presence of 100 μM deferoxamine caused a detectable increase in protoporphyrin IX-associated fluorescence, suggesting that lowering of the availability of iron, permits the accumulation of protoporphyrin IX and a reduction in the contraction to 5-HT. The presence of 100 μM deferoxamine did not appear to accelerate the time course of protoporphyrin IX accumulation or the amount formed from 100 μM ALA. After 8 h of organ culture, the BPA fluorescence in the presence of ALA (1015±79 AU) was not significantly increased from BPA exposed to 100 μM ALA+100 μM deferoxamine (939±137 AU, n=8), and the increased amount of ALA fluorescence observed after 24 h (1658±122 AU) was not also not significantly altered by the presence of deferoxamine (1404±153 AU).

Discussion

This study provides evidence that a previously identified activator of sGC, protoporphyrin IX, can function as an endogenous regulator of vascular function through cGMP. While most previous work with protoporphyrin IX was performed on purified sGC (19, 20, 34), there is an absence of evidence regarding relationships between protoporphyrin IX production in intact vascular tissue and how this pathway could function to regulate sGC. Exposure of isolated BPA under organ culture conditions to 50-100 μM doses of ALA increased protoporphyrin IX levels to amounts that decreased force in a manner that was associated with increased sGC activity and phosphorylation of VASP on the serine-239 site phosphorylated by cGMP-dependent protein kinase. The availability of Fe appeared to have a major role in controlling arterial levels of protoporphyrin IX and the ability of organ culture with ALA to suppress force generation. A model showing how ALA appears to control BPA force through generating a protoporphyrin DC-bound activated form of sGC is shown FIG. 6. This model compares the actions of protoporphyrin DC with the NO-binding $Fe^{2+}$ form of heme-containing sGC, because it appears to be the major form of sGC present in BPA under basal conditions (11).

The ability to increase protoporphyrin IX levels in the arterial ring segments was developed using an organoid culture technique. Since the surface fluorescence of protoporphyrin IX is routinely used as a method of monitoring its formation in multiple tissues for studies on cancer detection and phototherapy, this method was adapted for monitoring the levels of protoporphyrin DC in BPA ring segments. The data suggests that organ culture with 50-100 μM concentrations of the protoporphyrin IX precursor ALA led to increased protoporphyrin IX levels. Interestingly, there was an association between the limits of detecting statistically significant amounts of both ALA-elicited protoporphyrin IX generation and the force depressing actions of organ culture with ALA. An increase in the phosphorylation of VASP on its cGMP-associated serine-239 site was observed under the conditions where exposure of BPA to the 100 μM dose of ALA caused major decreases in contraction to serotonin. The effects of exposing organ cultured BPA to an NO donor during studies examining the contraction to 5-HT and changes in VASP phosphorylation were compared with the actions of ALA to examine if similarities existed in the magnitude of the responses observed. A dose of 10 μM spermine-NONOate caused a decrease in the contraction to 5-HT which was comparable with the decrease observed in BPA organ culture with 100 μM ALA, and both of these treatments produced similar increases in VASP phosphorylation. It has been previously demonstrated that purified sGC may bind and become activated by the addition of protoporphyrin IX through a process that appears to involve a time-dependent exchange of protoporphyrin IX with the $Fe^{2+}$ form of the heme present on sGC when it is isolated and kept under reducing conditions (16, 20, 34). The method of increasing protoporphyrin IX levels in BPA used in this study led to increased sGC activity in homogenates without detectable evidence for increased sGC expression, suggesting that at least some of the protoporphyrin IX remained bound to the sGC preparation used to determine its activity. Since the heme oxidant inhibitor of sGC activation did not significantly alter the force depressing actions or increase in VASP phosphorylation caused by organ culture with ALA, sGC activity was being increased by a process which was not dependent on stimuli inhibited by ODQ, such as NO and carbon monoxide (8, 29). Overall, these data support a role for ALA promoting relaxation through increasing the biosynthesis of protoporphyrin DC, which subsequently stimulates sGC to promote relaxation through processes controlled by cGMP-dependent protein kinase.

Iron availability appeared to have a major role in controlling the ability of ALA to promote increases in protoporphyrin IX and decreases in contraction to 5-HT. The presence of additional Fe (100 μM) during organ culture with ALA (100 μM) was observed to reverse the increase in protoporphyrin IX and force depressing effects caused by ALA. Since organ culture with Fe did not influence force generation or the detection of protoporphyrin IX, basal levels of protoporphyrin IX (in the absence of added ALA) are probably below the levels needed to alter the activity of sGC. In addition, exposure to Fe did not have secondary actions such as, altering contraction to 5-HT. Measurements of heme formation suggest that neither Fe nor ALA promoted significant increases in heme under the organ culture conditions examined. The absence of a detectable increase in heme in the presence of ALA suggests that limitations in the availability of Fe may have prevented the biosynthesis of heme from protoporphyrin IX. The absence of effects of Fe on heme, suggest that endogenous levels of ALA (in the absence of added ALA) are below the levels which would promote increased heme biosynthesis under organ culture conditions examined. The data also demonstrate a decrease in protoporphyrin IX detection in BPA organ cultured with ALA together with Fe was associated with the observance of increased heme in BPA, suggesting that Fe was promoting the conversion of protoporphyrin IX to heme. Interestingly, chelating iron with 100 μM deferoxamine led to increased detection of protoporphyrin IX in BPA organ cultured with 10 μM ALA, and a significantly inhibited level of force generation to 5-HT. These data suggest that Fe present in BPA under organ culture conditions was probably promoting the conversion of protoporphyrin IX synthesized from exogenous ALA to heme. The absence of detectable changes of heme in the presence of 100 μM ALA imply that either the levels of heme formed under these conditions were below the detection limits of the heme assay or that heme oxygenase further metabolized the heme that was formed. Since conditions of maximal heme generation (100 μM ALA+Fe) were associated with an absence of alterations in the contraction to 5-HT, carbon monoxide generated by the heme oxygenase reaction was not having a detectable effect on vascular function under the conditions examined. Observations that iron chelation did not increase basal levels of protoporphyrin IX or alter the contraction to 5-HT are also consistent with the absence of endogenous levels of protoporphyrin IX biosynthesis in amounts that could regulate vascular function under the conditions examined. Overall, these observations suggest that the availability of ALA is a key factor in controlling the biosynthesis of protoporphyrin IX in BPA, and that Fe availability has a major role influencing the levels of protoporphyrin IX that are observed as a result of its role in enabling the biosynthesis of heme. The influence of Fe availability on controlling the levels of protoporphyrin IX were closely associated with its effects on force generation by 5-HT, which further supports a role for protoporphyrin IX in controlling vascular function under the conditions examined.

The data in this study is consistent with increasing protoporphyrin IX biosynthesis from ALA resulting in sGC activation and a cGMP-elicited decrease in force generation. This mechanism may be a contributing factor to the decrease in systemic and pulmonary artery pressure seen in humans treated with ALA (13), because animal studies on the use of ALA in phototherapy for restenosis have observed (28) that protoporphyrin IX accumulates in the smooth muscle of arteries with a time course that is similar to its effects on blood pressure seen in the human study. The availability of iron is a major factor in determining if protoporphyrin IX is allowed to accumulate, or if it is converted to heme through the ferrochelatase reaction. Since heme competes with protoporphyrin IX for its binding site on sGC with a binding affinity for protoporphyrin IX in the low nanomolar concentration range and a binding affinity for heme of ~350 nM (34), endogenous heme could also function to attenuate sGC activation by protoporphyrin IX. In view of the fact that circulating levels of ALA are below the micromolar concentration range (7), cellular mechanisms controlling the biosynthesis of ALA and levels of protoporphyrin IX might be more important factors for identifying the physiological importance of the regulatory mechanism examined in this study. The influence of modulating iron availability in the absence of ALA suggests that endogenous ALA levels are below the amounts that could generate vasoactive levels of protoporphyrin IX in BPA. Iron levels seem to control the expression of ferrochelatase and the generation of heme (1, 32). Additionally, heme functions as a primary inhibitory regulator of the biosynthesis of ALA (10), and decreases in heme biosynthesis are associated with diseases of aging (3). Thus, genetic and/or metabolic conditions which disrupt the regulatory mechanisms of heme biosynthesis might allow the accumulation of protoporphyrin IX in amounts that alter multiple aspects of vascular function through stimulating sGC. Therefore, the regulation of vascular function through protoporphyrin IX is a physiologically-important regulatory mechanism under conditions where this heme precursor is allowed to accumulate. In addition, promoting protoporphyrin IX accumulation is a good therapeutic target for the treatment of vascular disease.

Example 2

Bovine bronchi were isolated from the same lungs used for pulmonary arteries, and studied for changes in protoporphyrin IX fluorescence and force under the same conditions as bovine pulmonary arteries described above. Superoxide was detected by the chemiluminescence produced by 5 μM lucigenin, which was detected by photon counting in a scintillation counter.

The rats were pretreated with 60 mg/kg ALA or with a saline vehicle (i.p.). After 24 hours they were anesthetized with 50 mg/kg sodium pentobarbital and the aorta was removed for in vitro studies. Isolated aortic rings were studied for changes in protoporphyrin IX fluorescence and force under the same conditions similar to those used for bovine pulmonary arteries described above, except that 1 gram of passive force was used.

ALA has a time-dependent effect on causing protoporphyrin IX accumulation and a prolonged relaxation of airway smooth muscle.

The data in FIG. 7A shows that organ culture of bovine bronchi (~3 mm diameter) with 0.1 mM ALA caused a time-dependent increase in protoporphyrin IX fluorescence in a manner similar to that seen in bovine arteries (See FIG. 1A). The data in FIG. 7B shows that organ culture with 0.1 mM ALA inhibits (relaxes) force generation to 10 µM acetylcholine (ACh) compared to airways organ cultured for 24 hrs in the absence of ALA. These data demonstrate that organ culture with ALA causes relaxation in bovine bronchial (airway) smooth muscle under conditions where it also causes protoporphyrin IX accumulation.

Demonstration that ALA can be used in vivo to promote a prolonged relaxation which is resistant to oxidant conditions.

Treatment of rats with a single dose of 60 mg/kg of ALA by i.p. injection results in the observation of increased in protoporphyrin IX fluorescence in endothelium-rubbed aorta compared to aorta from saline-injected control rats 24 hours after the treatment of the animals (FIG. 8A). Aorta from these animals show a decreased contraction to the protein kinase C activator 10 µM phorbol 11,12-dibutyrate (PDBu), a contractile agent that increases superoxide in multiple smooth muscle preparations, including the airway smooth muscle shown in (See FIG. 7C). Thus, ALA has a long lasting relaxing effect when it is injected in vivo, and increased aortic levels of protoporphyrin IX appear to be associated with the relaxation that is observed.

REFERENCES

1. Abraham N G, Camadro J M, Hoffstein S T, and Levere R D. Biochim Biophys Acta 870: 339-349, 1986.
2. Archer S L, Huang J M, Hampl V, Nelson D P, Shultz P J, and Weir E K. Proc Natl Acad Sci USA 91: 7583-7587, 1994.
3. Atamna H, Killilea D W, Killilea A N, and Ames B N. Proc Natl Acad Sci USA 99: 14807-14812, 2002.
4. Brune B and Ullrich V. Mol Pharmacol 32: 497-504, 1987.
5. Burstyn J N, Yu A E, Dierks E A, Hawkins B K, and Dawson J H. Biochemistry 34: 5896-5903, 1995.
6. Craven P A and DeRubertis F R. Biochim Biophys Acta 745: 310-321, 1983.
7. Dalton J T, Yates C R, Yin D, Straughn A, Marcus S L, Golub A L, and Meyer M C. Cancer J Pharmacol Exp Ther 301: 507-512, 2002.
8. Foresti R, Hammad J, Clark J E, Johnson T R, Mann B E, Friebe A, Green C J, and Motterlini R. Br J Pharmacol 142: 453-460, 2004.
9. Gerzer R, Bohme E, Hofmann F, and Schultz G. FEBS Lett 132: 71-74, 1981.
10. Granick S. J Biol Chem 241: 1359-1375, 1966.
11. Gupte S A, Rupawalla T, Phillibert D, Jr., and Wolin M S. Am J Physiol 277: L1124-1132, 1999.
12. Hassoun P M, Filippov G, Fogel M, Donaldson C, Kayyali U S, Shimoda L A, and Bloch K D. Am J Respir Cell Mol Biol 30: 908-913, 2004.
13. Herman M A, Webber I, Fromm D, and Kessel D. J Photochem Photobiol B 43: 61-65, 1998.
14. Hosein S, Marks G S, Brien J F, McLaughlin B E, and Nakatsu K. Can J Physiol Pharmacol 80: 761-765, 2002.
15. Iesald T, Gupte S A, and Wolin M S. Circ Res 85: 1027-1031, 1999.
16. Ignarro L J, Ballot B, and Wood K S. J Biol Chem 259: 6201-6207, 1984.
17. Ignarro L J, Burke T M, Wood K S, Wolin M S, and Kadowitz P J. J Pharmacol Exp Ther 228: 682-690, 1984.
18. Ignarro L J, Byrns R E, Buga G M, and Wood K S. Am J Physiol 253: H1074-1082, 1987.
19. Ignarro L J, Wood K S, and Wolin M S. Proc Natl Acad Sci USA 79: 2870-2873, 1982.
20. Ignarro L J, Wood K S, and Wolin M S. Adv Cyclic Nucleotide Protein Phosphorylation Res 17: 267-274, 1984.
21. Jenkins M P, Buonaccorsi G, MacRobert A, Bishop C C, Bown S G, and McEwan J R. Eur J Vasc Endovasc Surg 16: 284-291, 1998.
22. Johnson F K and Johnson R A. Am J Physiol Regul Integr Comp Physiol 285: R536-541, 2003.
23. Lincoln T M, Dey N, and Sellalc H. J Appl Physiol 91: 1421-1430, 2001.
24. Mansfield R, Bown S, and McEwan J. Heart 86: 612-618, 2001.
25. Mingone C J, Gupte S A, Ali N, Oeckler R A, and Wolin M S. Am J Physiol Lung Cell Mol Physiol 290: L549-557, 2006.
26. Mingone C J, Gupte S A, Iesald T, and Wolin M S. Am J Physiol Lung Cell Mol Physiol 285: L296-304, 2003.
27. Moesta K T, Ebert B, Handke T, Nolte D, Nowak C, Haensch W E, Pandey R K, Dougherty T J, Rinneberg H, and Schlag P M. Cancer Res 61: 991-999, 2001.
28. Nyamekye I, Anglin S, McEwan J, MacRobert A, Bown S, and Bishop C. Circulation 91: 417-425, 1995.
29. Schrammel A, Behrends S, Schmidt K, Koesling D, and Mayer B. Mol Pharmacol 50: 1-5, 1996.
30. Smits T, Robles C A, van Erp P E, van de Kerkhof P C, and Gerritsen M J. J Invest Dermatol 125: 833-9, 2005.
31. Stone J R and Marietta M A. Biochemistry 33: 5636-5640, 1994.
32. Taketani S, Adachi Y, and Nakahashi Y. Eur J Biochem 267: 4685-4692, 2000.
33. Tzao C, Nickerson P A, Russell I A, Gugino S F, and Steinhom R H. Pediatr Pulmonol 31: 97-105, 2001.
34. Wolin M S, Wood K S, and Ignarro L J. J Biol Chem 257: 13312-13320, 1982.

What is claimed is:

1. A method of inducing smooth muscle relaxation in a subject in need thereof comprising administering to the subject an effective amount of an agent having the property of promoting the accumulation of protoporphyrin IX in the smooth muscle, wherein the subject is a mammal.

2. The method of claim 1, wherein the subject is a human.

3. The method of claim 1, wherein the agent is selected from the group consisting of: δ-aminolevulinic acid, an ester, an amide, a metabolic precursor and a pharmaceutically acceptable salt thereof.

4. The method of claim 3, wherein the subject is a human.

5. The method of claim 4, wherein the smooth muscle is a non-vascular smooth muscle.

6. The method of claim 1, wherein the agent is δ-aminolevulinic acid.

7. The method of claim 6, wherein the subject is a human.

8. The method of claim 7, wherein the smooth muscle is a non-vascular smooth muscle.

9. The method of claim 3, further comprising administering to the subject an effective amount of an agent having the property of binding or chelating iron, promoting the accumulation of protoporphyrin IX and/or depleting cellular heme.

10. The method of claim 3, further comprising administering to the subject an effective amount of deferoxamine and/or ferritin.

11. A method of relaxing microvasculature in a subject in need thereof comprising administering to the subject an effective amount of an agent having the property of promoting the accumulation of protoporphyrin IX in the smooth muscle, wherein the subject is a mammal.

12. The method of claim 11, wherein the subject is a human.

13. The method of claim 11, wherein the agent is selected from the group consisting of: δ-aminolevulinic acid, an ester, an amide, a metabolic precursor and a pharmaceutically acceptable salt thereof.

14. The method of claim 13, wherein the subject is a human.

15. The method of claim 11, wherein the agent is δ-aminolevulinic acid.

16. The method of claim 15, wherein the subject is a human.

17. The method of claim 11, further comprising administering to the subject an effective amount of an agent having the property of binding or chelating iron, promoting the accumulation of protoporphyrin DC and/or depleting cellular heme.

18. The method of claim 17, wherein the subject is a human.

* * * * *